United States Patent [19]

Rue

[11] 4,077,898

[45] Mar. 7, 1978

[54] IODINE/PHOSPHATE ESTER COMPOSITIONS AND METHODS OF USING THEM

[75] Inventor: Larry M. Rue, Inver Grove Heights, Minn.

[73] Assignee: Economics Laboratory, Inc., St. Paul, Minn.

[21] Appl. No.: 759,654

[22] Filed: Jan. 17, 1977

Related U.S. Application Data

[63] Continuation-in-part of Ser. No. 738,004, Nov. 2, 1976, abandoned, which is a continuation-in-part of Ser. No. 544,389, Jan. 27, 1975, abandoned, which is a continuation-in-part of Ser. No. 62,727, Aug. 10, 1970, abandoned.

[51] Int. Cl.² .......................... C11D 3/48; C11D 7/36
[52] U.S. Cl. ........................................ 252/106; 134/2; 134/3; 134/22 R; 252/143; 252/153; 252/545; 252/548; 252/DIG. 17; 424/150
[58] Field of Search .................. 134/2, 3, 22 R, 22 C; 252/106, 143, 545, 548, DIG. 17; 424/150, 199, 224

[56] References Cited

U.S. PATENT DOCUMENTS

| | | | |
|---|---|---|---|
| 2,114,370 | 4/1938 | Bickenhauser | 424/233 |
| 2,679,533 | 5/1954 | Darragh et al. | 260/567.6 |
| 2,710,277 | 6/1955 | Shelanski et al. | 424/150 |
| 2,977,315 | 3/1961 | Scheib et al. | 252/106 |
| 3,004,056 | 10/1961 | Nunn et al. | 260/461 |
| 3,004,057 | 10/1961 | Nunn et al. | 260/461 |
| 3,028,301 | 4/1962 | Winicov | 424/150 |
| 3,028,427 | 4/1962 | Winicov | 260/567.6 |
| 3,029,183 | 4/1962 | Winicov | 424/150 |
| 3,061,506 | 10/1962 | Nunn et al. | 252/106 X |
| 3,326,806 | 6/1967 | Dolby | 252/106 |
| 3,513,098 | 5/1970 | Cantor et al. | 252/106 |
| 3,650,966 | 3/1972 | Bakka | 252/106 |
| 3,694,365 | 9/1972 | Castner | 252/106 |
| 3,728,157 | 4/1973 | Griparis | 134/22 R |

*Primary Examiner*—P.E. Willis, Jr.
*Attorney, Agent, or Firm*—Merchant, Gould, Smith, Edell, Welter & Schmidt

[57] ABSTRACT

Ethanolamine (preferably triethanolamine) salts of phosphate esters (i.e., phosphate esters of ethoxylated alcohols) are used as carrier or complexing agents for iodine (e.g., in preparing pre-surgical germicidal compositions). These solutions have "fast-draining" properties and are especially useful for sanitizing containers in automated or continuous-line operations.

12 Claims, No Drawings

IODINE/PHOSPHATE ESTER COMPOSITIONS AND METHODS OF USING THEM

CROSS-REFERENCE TO RELATED APPLICATIONS

This application is a continuation-in-part of my copending application Ser. No. 738,004, filed Nov. 2, 1976 now abandoned, which is a continuation-in-part of my copending application Ser. No. 544,389, filed Jan. 27, 1975 which is a continuation-in-part of my copending application Ser. No. 62,727, filed Aug. 10, 1970 both abandoned.

BACKGROUND OF THE INVENTION

During recent years, increasing interest has been given to the use of iodine as an antiseptic or germicide because of the discovery that iodine can be complexed and solubilized by many substances. Iodine complexes allow iodine to be released slowly to provide persistent germicidal properties without allowing the iodine concentration to become high enough to cause side effects such as skin irritation. Illustrative of the prior art in this field are the following U.S. Pats.:

| U.S. Pat. No. | Patentee | Issue Date |
| --- | --- | --- |
| 2,710,277 | Shelanski et al | June 7, 1955 |
| 3,061,506 | Nunn et al | October 30, 1962 |
| 3,326,806 | Dolby | June 20, 1967 |

One class of phosphate esters known to be useful as iodine complexing agents can be prepared by reacting $P_2O_5$ or its equivalent with condensation products of ethylene oxide and monohydric alcohols wherein the alcohols may contain from 6-24 carbon atoms and the number of moles of ethylene oxide in the condensation products can vary widely. Phosphate esters of this type, particularly those containing from 10-20 moles of ethylene oxide per mole of alcohol, are disclosed in the prior art as effective iodine carriers or complexing agents. However, such complexes have a tendency to produce intolerable amounts of foam for some uses. The foam produced has a tendency to be slow-draining. Thus while sanitizers of this type are very good for cleaning bottles and the like, beads of foam often remain in the container which makes it difficult to tell if the bottles are clean. Since it is difficult to tell if only foam is left or if other impurities are present, this is especially troublesome in automated or continuous, fast-moving line (production-line type) operations where the foam must drain cleanly from the bottles in the few seconds between sanitizing and filling. Moreover, phosphate esters of this general type form unstable complexes with iodine when the ethylene oxide/alcohol mole ratio is reduced much below 10 (e.g., reduced to 3:1).

The germicidal properties of iodine are reported to vary with pH, optimum germicidal activity occurring under strongly acidic conditions.

SUMMARY OF THE INVENTION

The present invention is based upon the discovery that certain low foaming phosphate esters will not complex iodine to any extent unless they are first partially neutralized with mono, di or triethanolamine. Once the iodine is complexed with a partially neutralized phosphate ester, the comlex may be reacidified without destabilizing the complex. An acidic phosphate ester is desirable in order to obtain maximum bactericidal performance when the concentrate is diluted with water to make the use solution. Moreover, the addition of the ethanolamine (preferably triethanolamine) to phosphate esters made from ethoxylated alcohols having a mole ratio of ethylene oxide to alcohol of less than 5:1 results in significantly improved storage stability of the resulting iodine complex.

After formation of the iodine complex, it can be diluted (e.g., with water and coupling solvents) and the pH adjusted downwardly by acid addition to improve germicidal activity without destroying the improved stability and low foaming characteristics.

The complexes of this invention are generally low foaming and "fast-draining," which makes them ideally suited to automated sanitization of containers.

DETAILED DISCUSSION

The Phosphate Esters

The phosphate esters useful in the practice of the present invention are the phosphate esters of the condensation products of ethylene oxide with $C_8$–$C_{18}$ (preferably $C_{10}$–$C_{14}$) acyclic monohydric alcohols. Saturated aliphatic alcohols, desirably straight chain alcohols, are preferred.

Procedures for condensing ethylene oxide with alcohols are well known and are disclosed in the literature (e.g., batch reactions in the presence of the basic condensation catalysts like KOH at elevated temperatures). Although the present invention can be applied to phosphate esters having a wide range of ethylene oxide/alcohol mole ratios (e.g., from 2-100 moles of ethylene oxide per mole of alcohol), the present invention finds particular utility in combination with lower foaming phosphate esters having ethylene oxide/alcohol mole ratios below 6:1, particularly from 2-4:1. These phosphate esters are not known to complex appreciable amounts of iodine.

Phosphate esters of such ethoxylated alcohols can be prepared by procedures known in the art which involve reacting the ethoxylated alcohol with $P_2O_5$ or its equivalent; see the aforementioned Nunn et al. U.S. Pat., No. 3,061,506, column 2, lines 37-53. Typically, the mole ratio of ethoxylated alcohol to $P_2O_5$ will be from 2-3:1, i.e., 1-1.5 moles of ethoxylated alcohol per mole of phosphate ester.

The resulting phosphate esters range from liquids to solids or semi-solids, depending upon the relative amounts of the various reactants that have been employed. Phosphate esters that are liquid at room temperature (i.e., liquid at 25° C.) are particularly useful.

Forming the Ethanolamine Salts

Although this description of procedure is directed to the use of triethanolamine, it should be understood that the same procedure applies for mono- or diethanolamine. The triethanolamine salts can be formed by addition to the phosphate ester of about one equivalent of triethanolamine per acid equivalent (the preferred phosphate esters contain 1.5-2 equivalents of ionizable or acid hydrogen). A strictly stoichiometric (equivalent-for-equivalent) reaction does not produce a pH of 7.0, since triethanolamine is a relatively weak base, its reported $pK_a$ being less than 10. Thus, an equivalent-for-equivalent neutralization reaction results in a pH, measured at 1 wt. % in aqueous solution, of about 6.0. This equivalent-for-equivalent (i.e., stoichiometric) neutralization provides a stable salt which can then be re-acidified for maximum germicidal activity.

Available data relating to this invention indicate that neutralization with mono-, di-, or triethanolamine is needed for the desired stable complexing of the iodine. The acidic (unneutralized) esters do not appear to form stable complexes with iodine. Furthermore, if the esters are neutralized with sodium or ammonium hydroxide, the resulting sodium or ammonium salts also form relatively unstable iodine complexes. Triethanolamine neutralization is particularly preferred for preparing iodine complexes which are easier to formulate and which have lower viscosity, better stability (e.g., freeze-thaw stability), and low foaming characteristics, although both diethanolamine and monoethanolamine also provide these desirable characteristics to a markedly greater extent than sodium or ammonium hydroxide. (Triethanolamine is also preferred for its low toxicity and negligible amine odor.)

For the purposes of this invention, substantially stoichiometric neutralization can be assumed to be attained when the pH of the neutralized ester in 1% aqueous solution is about six. Underneutralization (e.g., to a pH of 4.5 in 1% solution) can lead to stability problems for the iodine complex, though some iodine complexes are stable even when less than the stoichiometric amount of triethanolamine is present. Overneutralization (e.g., to a 1% pH of 7.6) can be even more undesirable, since substantial loss of iodine from the complex is likely. A moderate excess of triethanolamine (e.g., neutralization to about 6.5 or even 7.0) can be tolerated, however.

As is generally known in the chemical arts, a fairly precise neutralization to the end point (in this case to a pH in 1% solution of about 6) can be achieved with accurate pH monitoring and incremental addition of the base (i.e., the mono-,di-, or triethanolamine). The viscosity increases as the end point is approached, and the neutralized ester at a pH of 6.0 has a thick, greasy consistency. Dilution of the phosphate esters with water, instead of decreasing viscosity, actually increases it. To reduce viscosity and make mixing with iodine easier, hydrophilic organic solvents (e.g., the ethylene glycol monoethers such as the monobutyl ether) can be added in small amounts, as will be explained subsequently. These organic solvents are not needed for the aforementioned stability or low foaming properties, however.

Forming The Iodine Complexes

The iodine complexes can be prepared by simply mixing or adding iodine to the neutralized phosphate ester. Formation of the complex can be facilitated by the use of moderate heat (e.g., 65° C.) coupled with slow addition of the iodine and agitation of the resulting mixture. The amount of iodine used to make the complex is based upon the weight of the complexing agent, i.e., the neutralized phosphate ester. The germicidal activity of the complex is generally related to the amount of iodine it contains; however, an unduly large amount of iodine (e.g., more than 30% by weight, based on the weight of the neutralized ester, i.e., more than 43 parts per hundred) can adversely affect the stability of the complex. Good stability is obtained with amounts of iodine ranging up to 30%, e.g., 5-25% by weight, i.e., 5.3-33 phr. For optimum germicidal activity, amounts of iodine above 10% (11 phr) are preferred.

Forming Liquid Concentrates

After the iodine has been complexed with the alkanolamine neutralized phosphate ester, diluents, acids, and the like can be added to increase germicidal activity, reduce viscosity, or otherwise tailor the product for commercial use. A typical commercial product contains a substantial amount of water, but, in view of the significant amount of iodine/neutralized phosphate ester complex (e.g., 10-20 weight % of the total weight of product), the product is considered a "concentrate." While the concentrate is a good germicidal agent, in actual sanitizing operations, for cost reasons, the concentrate can be diluted with water to form a rinse solution or use solution containing as little as 0.1% by weight of the concentrate.

When viscosity-reducing, high boiling, hydrophilic organic solvents such as ethylene glycol monobutyl ether ("Butyl Cellosolve") are included in the concentrate, they should be used in amounts less than 5% by weight of the concentrate (e.g., up to 2% by weight) in order to avoid the possibility of stability problems (e.g., freeze-thaw stability).

The nature and the amount of acid included in the concentrate are not critical. For maximum germicidal activity, enough acid can be added to bring the pH back into the strong acid range, e.g., less than 1.0, determined on the full-strength concentrate. However, the concentrate is useful without acidification, e.g., at a pH of 6.0, determined on the full-strength concentrate. The desired stability and low foaming characteristics of the concentrate can be obtained with and without acidification. Of course, any hard water added to the concentrate to prepare the use solution could have an effect upon pH since most hard water is slightly alkaline. Thus, it is ordinarily preferred to have at least enough acid in the concentrate to compensate for possible alkalinity in the use solution. In the process of making the concentrate, the acid is preferably added last. Both inorganic acids (e.g. phosphoric) and organic acids (e.g., hydroxyacetic) can be used.

In summary, the concentrates of this invention are typically produced as follows:

(a) The mono-, di-, or triethanolamine (a liquid) is added to the phoshate ester until the end point is reached, at which point the neutralized ester is thick and greasy. The neutralization is approximately stoichiometric, resulting in a pH of at least 4.5 but not more than 7.0.

(b) About 5-30% by weight of iodine, based on the weight of the neutralized ester, is added to form the complex.

(c) Soft water is added to the complex to provide the commercial product, sometimes referred to as the "concentrate."

(d) To reduce viscosity, a suitable hydrophilic organic solvent can optionally be added to the concentrate.

(e) To compensate for an alkaline use environment, acid can optionally be added to reduce the pH below 6.0 but preferably not below 0.5.

Method Of Sanitizing Containers

In use, the highly desirable low foaming properties of the compositions of this invention are accompanied by another very desirable property known as "fast draining." "Fast draining" is an important advantage of use solutions containing the iodine-phosphate ester complexes of this invention. In automated sanitization of containers, e.g., bottles, with liquid germicidal agents, it is important to avoid both excessive foaming and slow draining of the foam generated during sanitization, e.g., foam generated by a spray rinsing of the interior of the container. Beads or buttons of foam must drain rapidly (e.g., within 30 seconds or less) from bottles being automatically sanitized so that they can be immediately inspected to determine if there is any residue in the bottles, which would require rejection. If the bottles are found to be free of residue, they can be used immediately, e.g., in an automated filling process. Germicidal rinse solutions produced according to this invention can be formulated to drain from an inverted glass bottle in 20 seconds or less, in some cases almost instantaneously.

One method of sanitizing bottles (or other containers) with the composition of this invention is to:

(a) Fill the containers with a caustic solution, e.g., by running the containers through a soak tank;

(b) Allow the caustic solution to drain out through an opening in the container, essentially by means of a gravity flow, e.g., removing the containers from a soak tank in an inverted position (or inverting them subsequent to soaking) so that the caustic solution will drain out;

(c) Spray a use solution of the iodine-phosphate ester complex of this invention into the inverted containers; and (d) Allow the use solution to drain out through an opening in the container, essentially by means of a gravity flow.

One or more additional rinsing steps (e.g., a power rinse and a final rinse, both of which can be spray rinses with plain water or the like) can also be included in accordance with the conventional practice. With the "fast draining" complexes of this invention draining step (d) requires only a few seconds (e.g., 20 seconds or less). This invention is thus particularly well suited for an automated production line type of sanitizing operation.

The present invention will be further understood by reference to the following specific Examples.

EXAMPLES 1-6

In the following Examples, various phosphate esters were employed. Those phosphate esters were formed by reacting $P_2O_5$ with ethoxylated alcohols. The ethoxylated alcohols were prepared by conventional methods from a mixture of $C_{10}$-$C_{14}$ straight-chain, saturated, monohydric alcohols using approximately 2-4 moles of ethylene oxide per mole of alcohol. The amount of ethoxylated alcohol used per mole of $P_2O_5$ varied from Example to Example and is shown in Table I which follows. In each Example, the phosphate ester was neutralized by addition of triethanolamine to the pH shown in the Table.

For purposes of comparison, various test procedures were repeated using sodium hydroxide instead of triethanolamine as a neutralizing agent for the phosphate esters.

In each Example (and control), iodine was added to the phosphate ester (after neutralization, if appropriate) by thorough mixing. The resulting mixture was then diluted with water and a coupling solvent (butyl cellosolve). The pH was reduced by acid addition to obtain improved germicidal activity. Each Example and control was formulated into a liquid concentrate as follows:

| FORMULA OF LIQUID CONCENTRATES | |
|---|---|
| phosphate, with or without neutralization | 12.97 |
| iodine | 2.60 |
| water, soft | 53.40 |
| butyl cellosolve | 2.00 |
| 75% phosphoric acid | 8.97 |
| 70% hydroxyacetic acid | 20.06 |
| TOTAL | 100.00 wt. % |

The results which were obtained are summarized in Table I which follows.

From the data of Table I, it can be seen that the addition of triethanolamine to the phosphate ester prior to formation of the iodine complex reduces foaming and improves storage stability. Other tests have shown that the liquid concentrates of the present invention can be used at higher use concentrations (e.g., 25 ppm iodine in machine rinse solutions) than certain commercially available liquid concentrates based on triethanolamine-free iodine complexes.

TABLE I

| Example No.[1] | Moles of Ethoxylated Alcohol per Mole of $P_2O_5$ | pH[3] | Storage Stability[4] Percent Available After (No. of Days): | | | | | | Foam Test[5] (Inches) | | Initial Overnight Stability | Freeze-Thaw Test | | Final Iodine Content |
|---|---|---|---|---|---|---|---|---|---|---|---|---|---|---|
| | | | 1 | 2 | 4 | 5 | 8 | 15 | During | After | | 1st Cycle | 2nd Cycle | |
| 1 | 3 | 4.5 | | | | | | | | | Unstbl. | | | |
| 2 | 2.75 | 4.5 | | 1.8 | 1.8 | | | | ⅛ | ⅛ | Stbl. | Slt.Ppt. | Slt.Ppt. | 1.9 |
| 3 | 2.5 | 4.5 | | 1.8 | 1.8 | | | | ⅛ | ⅛ | Stbl. | Stbl. | Stbl. | 1.9 |
| 4 | 3 | 6.0 | | | 1.9 | | 1.9 | 1.9 1.9 | ⅛ | ⅛ | Stbl. | Stbl. | Stbl. | 1.9 |
| 5 | 2.75 | 6.0 | | | 2.0 | | 1.9 | 1.9 1.8 | ⅛ | ⅛ | Stbl. | Stbl. | Stbl. | 1.9 |
| 6 | 2.5 | 6.0 | | | 2.0 | | 1.9 | 1.9 1.9 | ⅛ | ⅛ | Stbl. | Stbl. | Stbl. | 2.0 |
| Control 1[2] | 3 | | 1.0 | | 0.9 | | | | ⅛ | ⅛ | Possible Slt.Ppt. | Iod.Ppt. | Iod.Ppt. | 1.0 |
| Control 2 | 2.75 | | 1.1 | | 1.0 | | | | ⅛ | ⅛ | Possible Slt.Ppt. | Iod.Ppt. | Iod.Ppt. | 1.0 |
| Control 3 | 2.5 | | 1.1 | | 1.0 | | | | ⅛ | ⅛ | Possible Slt.Ppt. | Iod.Ppt. | Iod.Ppt. | 1.0 |
| Control 4 | 3 | 6.0 | | 1.8 | | | | 1.6 | ⅛ | ⅛ | Possible Slt.Ppt. | Iod.Ppt. | Iod.Ppt. | 1.7 |
| Control 5 | 2.75 | 6.0 | | 1.7 | | | 1.5 | 1.5 | ⅛ | ⅛ | Possible Slt.Ppt. | Iod.Ppt. | Iod.Ppt. | 1.5 |
| Control 6 | 2.5 | 6.0 | | 1.7 | | | 1.5 | 1.5 | ⅛ | ⅛ | Possible Slt.Ppt. | Iod.Ppt. | Iod.Ppt. | 1.5 |

[1]Controls 1-3 were unneutralized phosphate ester
[2]Controls 4-6 were neutralized with sodium hydroxide to pH 6
[3]pH of complex at 1 wt.% concentration
[4]Storage stability of liquid concentrates as measured by thiosulfate titration.
[5]A recirculating foam test (dynamic) using a three minute cycle.
[6]See Note A

EXAMPLE 7

The procedure of Examples 1-6 was repeated using a triethanolamine salt of a phosphate ester made from a six mole ethylene oxide adduct of mixed $C_{10}$-$C_{12}$ alcohol (the adduct is commercially available in the U.S.A. under the trademark "ALFONIC 1012-6"). The mole ratio of ethoxylated alcohol to $P_2O_5$ was 2:1. The amount to TEA used was sufficient to raise the pH to 6.0. Tests were conducted on the liquid concentrate (see Examples 1-6) with the following results:

| Test Results | |
|---|---|
| initial iodine (after forming concentrate) | 2.34% |
| iodine level after 11 days | 2.14% |
| foam height, during test | 3¾ inches |
| foam height, after test | 5 inches |
| freeze-thaw test, after 11 cycles | 2.14% iodine |

While the concentrate showed good storage and freeze-thaw stability, foaming was high, that is, too high for uses which require a low-foaming concentrate.

From the foregoing description and Examples 1-7, it can be appreciated that the use of triethanolamine salts offers an advantage over prior art techniques, particularly in the area of improved stability. Although the effect of triethanolamine on foaming is not always pronounced, the tendency is for foaming to be reduced.

EXAMPLE 8

The purpose of this Example was to investigate the effect of varying the amount of "Butyl Cellosolve" (ethylene glycol monobutyl ether) in the liquid concentrate formula of Example 6. The investigation was conducted by varying the liquid concentrate formula in two ways:

(1) omitting the Butyl Cellosolve completely and replacing it with 2.00% soft water, and (2) increasing the amount of Butyl Cellosolve to 5.00% and reducing the amount of soft water in the formula to 50.40%.

The pH of the resulting liquid concentrates was measured at full (100%) stength, i.e., without further dilution of the liquid concentrate formula. The sample liquid concentrates were also tested for stability and foaming characteristics. The stability of the concentrate containing 0% Butyl Cellosolve was virtually identical to that of Example 6, in both the freeze-thaw stability test (passed 5 cycles without separation) and the available iodine test. The sample containing 5% Butyl Cellosolve separated after 1 day of storage at room temperature, however, and was therefore considered unstable. This apparently high degree of instability was confirmed by the available iodine test. In a foaming test, the 0% Butyl Cellosolve sample again performed about as well as Example 6. A foam test was not attempted for the 5% Butyl Cellosolve sample because of its unacceptable stability. The results of the full strength or 100% pH measurements were as follows:

| Butyl Cellosolve Content | pH at 100% Concentration |
|---|---|
| 0% | 0.5 |
| 2% (Example 6) | 0.6 |
| 5%, upper phase: | 1.1 |
| phases mixed together: | 1.0 |

The principal advantage of Example 6 over the 0% Butyl Cellosolve sample was the somewhat lower viscosity, as indicated in the comparison below:

| Butyl Cellosolve Content | Viscosity, No. 2 Zahn at 75° F. |
|---|---|
| 0% | 60 seconds |
| 2% (Example 6) | 34 seconds |

EXAMPLE 9

The purpose of this Example was to investigate the effect of various bases used as neutralizing agents for the phosphate ester. For convenience of comparison, the ester was considered neutralized when a 1.0 wt.-% aqueous solution of the neutralized ester attained a pH of 6. The three bases used in this investigation were ammonium hydroxide ($NH_4OH$), monoethanolamine (hereinafter referred to as MEA) and diethanolamine (DEA). Iodine complexes were made in the manner described in the previous Examples, using the liquid concentrate formula of Examples 1-6. It was found that foaming was slightly greater, as compared to Example 6, for the samples neutralized with MEA and DEA. Due to its instability, a foaming test was not attempted for the sample neutralized with ammonium hydroxide. Results of a freeze-thaw test, an available iodine test, and a 100% (full strength) pH test are given below.

| Base Used for Neutralization | Freeze-Thaw Test | | |
|---|---|---|---|
| $NH_4OH$ | The concentrate separated after one day storage at room temperature | | |
| DEA | Passed 4 cycles with no separation | | |
| MEA | Passed 4 cycles with no separation | | |
| Base Used for Neutralization | Available Iodine | | |
| | Initial | After 7 Days | 100% pH |
| $NH_4OH$ | 2.14% | 0.01%* | 1.1*<br>1.4** |
| DEA | 2.01% | 1.91% | 0.7 |
| MEA | 2.15% | 1.97% | 0.9 |

*Determined on the upper phase of the separated concentrate.
**Determined on a mixed sample.

EXAMPLE 10

The purpose of this Example was to investigate the effect of varying the iodine content in the liquid concentrate formula of Example 6. The investigation was conducted by preparing three iodine/neutralized phosphate ester complexes following the formula of Example 6 except that the amount of iodine in the three complexes, based on the weight of neutralized phosphate ester, was 5%, 25%, and 30%; these three complexes are hereinafter referred to as 10-5, 10-25 and 10-30, respectively. To make the 10-5 (5%) complex, 95.23 parts by weight of neutralized phosphate ester were combined with 4.77 parts by weight of iodine; for the 10-25 complex, 80.01 parts by weight of neutralized ester were combined with 19.99 parts by weight of iodine; and for the 10-30 complex; it was 76.93 parts of neutralized ester and 23.07 parts of iodine. The basic formula was adjusted so that the amount of phosphate ester in each concentrate was the same. The percentages of Butyl Cellosolve, phosphoric acid, and hydroxyacetic acid remained at 2.0%, 8.97%, and 20.06%, respectively; the percentages of water and the three complexes are given below.

10-5 Concentrate: 55.35% water + 13.62% of the 10-5

-continued

| | complex. |
|---|---|
| 10-25 Concentrate: | 52.76% water + 16.21% of the 10-25 complex. |
| 10-30 Concentrate: | 52.11% water + 16.86% of the 10-30 complex. |

Tests were conducted as in Examples 8 and 9. The results were:

| | | Available Iodine | |
|---|---|---|---|
| Concentrate | Freeze-Thaw | Initial | After 14 Days |
| 10-5 (5%) | Passed (5 cycles) | 0.406% | 0.367% |
| 10-25 (25%) | Passed (5 cycles) | 2.25% | 2.12% |
| 10-30 (30%) | Unstable even at room temp. | 2.79% | 0.129%, determined on upper phase |

Although the concentrate with 30% iodine (based on the weight of the neutralized phosphate ester) was unstable, stability can be achieved by careful selection of the chain length of the alkyl group and the oxyethylene content of the ethoxylated alcohol as well as the alcohol ethoxylate/$P_2O_5$ ratio.

In tests for fast draining, it was found that the ethylene oxide content could have particularly interesting effects. For example, two concentrates similar to Example 6 and precisely identical except for ethylene oxide (EO) content had different draining rates, the concentrate containing 2 moles of EO per mole of alcohol being much faster draining than the corresponding concentrate containing 4 moles of EO per mole of alcohol.

EXAMPLE 11

Several samples of liquid concentrate having about 2 moles of ethylene oxide per mole of alcohol were prepared using the formula of Example 6 and tested for drainage time. The test involved spraying a use solution of 15 ppm available iodine into an inverted glass bottle (i.e., a "Coke" bottle) and measuring the time required for the last bubble of foam to drain from the bottle. The temperature of the solution was maintained at 55-65° C. and a spray pressure of 40 psi was used. The test cycle involved: (1) spraying the use solution into the inverted bottle for 3 seconds, (2) turning the spray off for 3 seconds, (3) turning the spray on for 3 seconds, (4) turning the spray off, (5) removing the bottle from the spray apparatus in an inverted position and allowing the foam to drain. The drainage time was the period from when the spray was turned off until the foam drained completely. With all the samples the bottles drained virtually instantaneously (i.e. the foam drained almost before the bottle could be removed from the spray apparatus).

Several samples of liquid concentrates having about 4 moles of ethylene oxide per mole of alcohol were prepared using the formulas of Examples 4, 5 and 6 and were tested for drainage time using the same procedure. Some of the samples were "fast-draining" (i.e., less than 20 seconds) while other samples were "slow-draining" (i.e., more than 20 seconds). All samples of these liquid concentrates were found to be relatively fast-draining as compared to similar concentrates containing nonionic surfactants instead of the triethanolamine neutralized phosphate esters. For example, the same basic concentrate formula was put through the same five-step spray test with the exception that the triethanolamine-neutralized phosphate ester was replaced by a variety of surfactants including a polyalkylene glycol ether and several polyoxyethylene polyoxypropylene block polymers. All of these formulas were found to be slow-draining, generally taking one or even two minutes to drain.

What is claimed is:

1. A method for sanitizing containers with a storage stable liquid composition having germicidal properties, said liquid composition comprising:
  (a) a phosphate ester of ethoxylated $C_8$-$C_{18}$ saturated aliphatic monohydric alcohol, which ester has been neutralized with an approximately stoichiometric number of equivalents of at least one ethanolamine selected from the group consisting of mono-, di-, and triethanolamine to a pH of 4.5-7.0 determined on a 1% aqueous solution, said ethoxylated alcohol containing 2-4 moles of ethylene oxide per mole of alcohol, each mole of said phosphate ester containing 1-1.5 moles of ethoxylated alcohol; and
  (b) 5-30% by weight of iodine, based on the weight of said ethanolamine neutralized phosphate ester; and
  (c) water, comprising the steps of:
    (1) contacting the interior surfaces of said containers with said liquid composition; and
    (2) draining said liquid composition from said containers, through an opening in said containers, essentially by means of a gravity flow.

2. The method of claim 1 where said containers are in a generally inverted position during said contacting step and said contacting is accomplished by spraying said liquid composition into said generally inverted containers.

3. The method of claim 1 wherein said ethanolamine is triethanolamine.

4. The method of claim 3, wherein said liquid composition has been reduced in viscosity by adding a viscosityreducing amount of less than 5% by weight, based on the weight of said liquid composition, of ethylene glycol monobutyl ether.

5. The method of claim 3 wherein said liquid composition has been acidified to a pH of less than 4.5.

6. The method of claim 5, wherein said liquid composition has been acidified with an acid selected from the group consisting of phosphoric acid and hydroxyacetic acid.

7. The method of claim 5, wherein said ethoxylated alcohol is a 2-4 mole ethylene oxide adduct of $C_{10}$-$C_{14}$ alcohol.

8. The method of claim 1, wherein said draining step is completed within 20 seconds or less for each container.

9. The method of claim 1, wherein said contacting step is applied to a series of continuously conveyed containers, and each said container is in an inverted position during said draining step, thereby facilitating said draining step.

10. The method of claim 1 wherein said ethoxylated alcohol contains about 2 moles of ethylene oxide per mole of alcohol.

11. The method of claim 5 wherein said ethoxylated alcohol contains about 2 moles of ethylene oxide per mole of alcohol and the draining of said containers is completed within 20 seconds or less for each container.

12. A method for making a storage stable, liquid composition having germicidal properties, said method comprising the steps of:

(a) neutralizing a phosphate ester of ethoxylated $C_8$-$C_{18}$ saturated aliphatic monohydric alcohol, said ethoxylated alcohol containing 2–4 moles of ethylene oxide per mole of alcohol, each mole of said phosphate ester containing 1–1.5 moles of ethoxylated alcohol, said neutralizing being carried out with an approximately stoichiometric number of equivalents of triethanolamine, whereby the pH of the resulting neutralized phosphate ester, when determined in 1% aqueous solution, is about 6;

(b) adding 5–30% by weight of iodine, based on the weight of said neutralized phosphate ester, to said neutralized phosphate ester, whereby said iodine is stably complexed by said neutralized phosphate ester;

(c) diluting the product of step (b) with water;

(d) reducing the viscosity of the product of step (c) by adding up to 5% by weight, based on the weight of the product of step (c), of ethylene glycol monobutyl ether; and (e) lowering the pH of the product of step (d) to less than 6.0 but more than 0.5 with at least one acid selected from the group consisting of phosphoric acid and hydroxyacetic acid.

* * * * *

UNITED STATES PATENT AND TRADEMARK OFFICE
CERTIFICATE OF CORRECTION

PATENT NO. : 4,077,898

DATED : March 7, 1978

INVENTOR(S) : Larry M. Rue

It is certified that error appears in the above-identified patent and that said Letters Patent are hereby corrected as shown below:

In the last heading of Table I, column 6, line 46 et seq., ("Final Iodine Content"), for "Content" read --Content$^6$--.

In the last line of Table 1, columns 5 and 6, for "See Note A" read --See Note 4--.

In column 10, line 23, for
"(c) water, comprising the steps of:"
read
--(c) water,
comprising the steps of:--

In column 10, line 38, for "cosityreducing" read --cosity-reducing--.

Signed and Sealed this

Tenth Day of October 1978

[SEAL]

Attest:

RUTH C. MASON
*Attesting Officer*

DONALD W. BANNER
*Commissioner of Patents and Trademarks*